United States Patent [19]

Knüppel et al.

[11] Patent Number: 5,234,899
[45] Date of Patent: Aug. 10, 1993

[54] SUBSTITUTED 2,2-DIFLUORO-1,3-BENZODIOXYL-4-KETONE HERBICIDES

[75] Inventors: Peter C. Knüppel, Wermelskirchen; Albrecht Marhold, Leverkusen; Thomas P. Hausner, Cologne; Hans-Joachim Santel, Leverkusen; Klaus Lürssen; Robert R. Schmidt, both of Bergisch-Gladbach; Heinz-Wilhelm Dehne, Monheim, all of Fed. Rep. of Germany

[73] Assignee: Bayer Aktiengesellschaft, Leverkusen, Fed. Rep. of Germany

[21] Appl. No.: 798,671

[22] Filed: Nov. 26, 1991

[30] Foreign Application Priority Data

Dec. 14, 1990 [DE] Fed. Rep. of Germany ....... 4040021

[51] Int. Cl.$^5$ .................. A01N 43/30; C07D 317/46
[52] U.S. Cl. ................................. 504/296; 549/436
[58] Field of Search .................... 71/88; 549/436; 504/140, 296

[56] References Cited

FOREIGN PATENT DOCUMENTS 0005756 12/1979 European Pat. Off. .

Primary Examiner—Nicky Chan
Attorney, Agent, or Firm—Sprung Horn Kramer & Woods

[57] ABSTRACT

The invention relates to novel substituted 2,2-difluoro-1,3-benzodioxyl-4-ketones of the general formula (I)

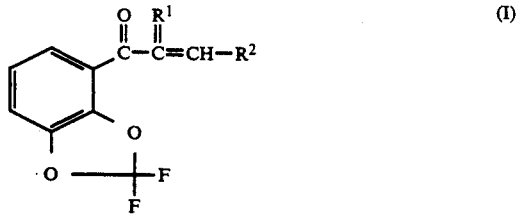

in which
R$^1$ represents a group from the series comprising —CN; —CO$_2$R$^5$ or

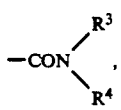

where
R$^3$ and R$^4$ in each case independently of one another represent hydrogen, alkyl, alkenyl, alkylcarbonyl, formyl or optionally substituted aralkyl,
R$^5$ represents alkyl and
R$^2$ represents a group from the series comprising

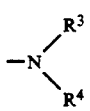

or —OR$^3$,
where R$^3$ and R$^4$ have the abovementioned meaning, a process for their preparation and their use as plant protection agents, in particular as herbicides.

7 Claims, No Drawings

SUBSTITUTED 2,2-DIFLUORO-1,3-BENZODIOXYL-4-KETONE HERBICIDES

The present invention relates to novel 2,2-difluoro-1,3-benzodioxyl-4- ketones, a process for their preparation, and their use as plant protection agents, in particular as herbicides.

It has already been disclosed that certain substituted acrylonitrile derivatives have herbicidal properties (compare DE-OS (German Published Specification) 2,330,913).

However, the herbicidal action of these compounds is not entirely satisfactory in all fields of application, in particular when low amounts and concentrations are applied.

Novel substituted 2,2-difluoro-1,3-benzodioxyl-4-ketones of the general formula (I)

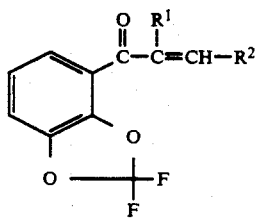

in which $R^1$ represents a group from the series comprising —CN; —CO$_2$R$^5$ or

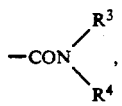

where
$R^3$ and $R^4$ in each case independently of one another represent hydrogen, alkyl, alkenyl, alkylcarbonyl, formyl or optionally substituted, aralkyl,
$R^5$ represents alkyl and
$R^2$ represents a group from the series comprising

or —OR$^3$,
where $R^3$ and $R^4$ have the abovementioned meaning, have been found.

Furthermore, it has been found that the novel substituted 2,2-difluoro-1,3-benzodioxyl-4-ketones of the general formula (I)

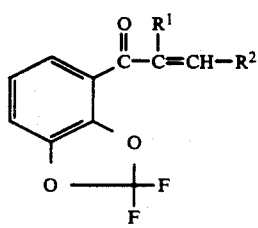

in which $R^1$ and $R^2$ have the abovementioned meanings, are obtained when the acid chloride of the formula (II)

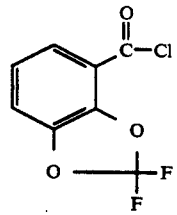

is reacted with substituted acrylic acid derivatives of the formula (III)

$$R^1—CH=CH—R^2 \quad\quad (III)$$

in which $R^1$ and $R^2$ have the abovementioned meanings, if appropriate in the presence of a diluent and if appropriate in the presence of a base.

Finally, it has been found that the novel substituted 2,2-difluoro-1,3-benzodioxyl-4-ketones of the formula (I) have a very good herbicidal activity.

Unless defined otherwise, preferred meanings in the general formulae are as follows:

Alkyl, on its own or in compound radicals,
straight-chain or branched alkyl having 1 to 6, in particular 1 to 4, carbon atoms. The following may be mentioned by way of example and as preferred: methyl, ethyl, n- or i-propyl and n-, i-, s- and t-butyl.

Alkenyl
straight-chain or branched alkenyl having preferably 2 to 6, particularly preferably 2 to 4, and in particular 3, carbon atoms. The following may be mentioned by way of example: vinyl, allyl, prop-2-enyl, but-1-enyl, 2-butenyl, 3-butenyl and 1-methallyl.

Aryl
unsubstituted or substituted aryl having 6 to 10 carbon atoms. The following may be mentioned by way of example and as preferred: in each case unsubstituted or substituted phenyl and naphthyl, in particular unsubstituted or substituted phenyl.

Formula (I) provides a general definition of the novel substituted 2,2-difluoro-1,3-benzodioxyl-4-ketones according to the invention. Preferred compounds of the formula (I) are those in which
$R^1$ represents a group from the series —CN; —CO$_2$R$^5$ or

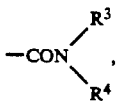

where
$R^3$ and $R^4$ in each case independently of one another represent hydrogen, straight-chain or branched alkyl having 1 to 4 carbon atoms, straight-chain or branched alkenyl having 2 to 4 carbon atoms, straight-chain or branched alkylcarbonyl having 1 to 4 carbon atoms, formyl, or benzyl which optionally monosubstituted or disubstituted by fluorine, chlorine, bromine, methyl, methoxy, trifluoromethyl or trifluoromethoxy and
$R^5$ represents straight-chain or branched alkyl having 1 to 4 carbon atoms and $R^2$ represents a group from the series comprising

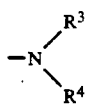

or —$OR^3$, where $R^3$ and $R^4$ have the abovementioned meanings

Very particularly preferred compounds of the formula (I) are those in which $R^1$ represents a group from the series —CN; —$CO_2R^5$ or

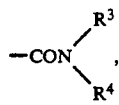

where
$R^3$ and $R^4$ in each case independently of one another represent hydrogen, methyl, ethyl, n- or i-propyl, vinyl, allyl, methylcarbonyl, ethyl-carbonyl, formyl or benzyl and
$R^5$ represents methyl or ethyl and
$R^2$ represents a group from the series comprising

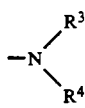

where $R^3$ and $R^4$ have the abovementioned meaning.

The following substituted 2,2-difluoro-1,3-benzodioxyl-4-ketones of the general formula (I) may be mentioned individually in addition to the compounds mentioned in the Preparation Examples:

TABLE 1

| $R^1$ | $R^2$ |
|---|---|
| CN | —NHCH$_3$ |
| CN | —NH—C(=O)—CH$_3$ |
| CN | —NH—C$_2$H$_5$ |
| CN | —N(C$_2$H$_5$)(C$_2$H$_5$) |
| CN | —NH$_2$ |
| CN | —NH—CH$_2$—C$_6$H$_5$ |

TABLE 1-continued

| $R^1$ | $R^2$ |
|---|---|
| CO$_2$CH$_3$ | —N(CH$_3$)(CH$_3$) |
| CO$_2$C$_2$H$_5$ | —N(CH$_3$)(CH$_3$) |
| CO$_2$NH$_2$ | —N(CH$_3$)(CH$_3$) |
| CO$_2$CH$_3$ | —N(CH$_3$)(CH$_3$) |

If, for example, 2,2-difluoro-1,3-benzodioxol-4-carboxylic acid chloride and N,N-dimethylaminoacrylonitrile are used as starting substances and trimethylamine as the base, the process according to the invention can be outlined by the following equation:

The acid chloride of the formula (II) to be used as starting substance in the process according to the invention is novel, but can be obtained by generally known and conventional processes, when the carboxylic acid of the formula (IV)

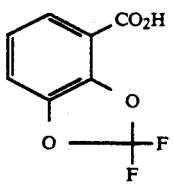 (IV)

is heated with halogenating agents such as, for example, thionyl chloride or oxalyl dichloride, if appropriate in the presence of a diluent such as, for example, benzene, at temperatures between 50° C. and 100° C., if appropriate in the presence of a nitrogen atmosphere (compare, for example, "Reaktionen und Synthesen im organisch-chemischen Praktikum" [Reactions and Syntheses in the Organochemical Laboratory Practical], L. -F. Tietze, T. Eicher, Georg Thieme Verlag Stuttgart, New York 1981).

The carboxylic acid of the formula (IV) is known (compare EP-OS (European Published Specification) 0,333,658).

Formula (III) provides a general definition of the substituted acrylic acid derivatives of the formula (III) furthermore to be used for carrying out the process according to the invention. In formula (III) $R^1$ and $R^2$ preferably, or in particular, have the meanings which have already been mentioned in connection with the description of the compounds of the formula (I) according to the invention as being preferred, or as particularly preferred, for $R^1$ and $R^2$. The compounds of the formula (III) are generally known compounds of organic chemistry.

The process according to the invention for the preparation of the novel substituted 2,2-difluoro-1,3-benzodioxyl-4-ketones of the formula (I) is preferably carried out using diluents. Suitable diluents for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile, and propionitrile, amides such as, for example, dimethylformamide, dimethylacetamide and N-methylpyrrolidone, and also dimethyl sulphoxide, tetramethylene sulphone and hexamethylphosphoric triamide.

Acid acceptors which can be employed in the process according to the invention are all acid-binding agents which can normally be used for reactions of this type. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates such as sodium carbonate, sodium hydrogen carbonate, potassium carbonate or potassium hydrogen carbonate, and also calcium carbonate, alkali metal acetates such as sodium acetate and potassium acetate, alkali metal alcoholates such as sodium methylate, sodium ethylate, sodium propylate and sodium isopropylate, sodium butylate, sodium isobutylate, sodium tert-butylate, potassium methylate, potassium ethylate, potassium propylate, potassium isopropylate, potassium butylate, potassium isobutylate and potassium tert-butylate, furthermore basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methylpyridine, 1,5-diazabicyclo-[4,3,0]-non-5-ene (DBN), 1,8-diazabicyclo-5,4,0]-undec-7-ene (DBU) and 1,4-diazabicyclo-[2,2,2]-octane (DABCO).

When carrying out the process according to the invention, the reaction temperatures can be varied within a substantial range. In general, the process is carried out at temperatures between 0° C. and 120° C., preferably at temperatures between 60° C. and 100° C.

For the carrying out the process according to the invention, the starting substances required in each case are generally employed in approximately equivalent amounts. However, it is also possible to use one of the two components employed in each case in a substantial excess. In general, the reactions are carried out in a suitable diluent in the presence of an acid acceptor, and the reaction mixture is stirred for several hours at the particular temperature required. Working-up in the process according to the invention is carried out in each case by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations( tea plantations, rubber plantations, oil palm plantations, cocoa plantations, soft fruit plantings and hopfields, and for the selective combating of weeds in annual cultures.

In this context, the active compounds of the formula (I) according to the invention are particularly suitable for selectively combating monocotyledon and dicotyledon weeds in monocotyledon and dicotyledon crops, using the pre-and post-emergence methods.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible. Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin -5(4H)-one (METRIBUZIN) for combating weeds in soya beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2',6'-diethyl-N-methoxymethylacetanilide (ALACHLOR); methyl-6,6-dimethyl-2,4-dioxo-3-[1-(2-propenyloxyamino)-butylidene]-cyclohexanecarboxylic acid(ALLOXYDIM);4-amino-benzenesulphonylmethylcarbamate (ASULAM); 2-chloro-4-ethylamino-6-isopropylamino-1,3,5-triazine (ATRAZINE); methyl 2-[[[[(4,6-dimethoxypyrimidine-2-yl)-amino]-carbonyl]-amino]-sulphonyl]-methyl]-benzoate (BENSULFURON); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitril (BROMOXYNIL); N-(butoxymethyl)-2-chloro-N-(2,6-diethylphenyl)-acetamide (BUTACHLOR); 5-amino-4-chloro-2-phenyl-2,3-dihydro-3-oxypyridazine (CHLORIDAZON); ethyl 2-{[(4-chloro-6-methoxy-2-pyrimidinyl)-aminocarbonyl]-aminosulphonyl}-benzoate (CHLORIMURON); N-(3-chlorophenyl)-isopropylcarbamate (CHLORPROPHAM); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); exo-1-methyl-4-(1-methylethyl)-2-(2-methylphenyl-methoxy)-7-oxabicyclo-(2,2,1)-heptanane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); N,S-diethyl N-cyclohexylthiocarbamate (CYCLOATE); 2-[1-(ethoximino)-butyl]-3-hydroxy-5-[tetrahydro-(2H)-thiopyran -3-yl]-2-cyclohexen-1-one (CYCLOXYDIM); 2-[4-(2,4-dichlorophenoxy)-phenoxy]-propionic acid, its methyl ester or its ethyl ester (DICLOFOP); 2-[(2-chlorophenyl)-methyl]-4,4-dimethylisoxazolidin-3-one (DIMETHAZONE); S-ethyl N,N-di-n-propyl-thiocarbamidate (EPTAME); 4-amino-6-t-butyl-3-ethylthio-1,2,4-triazin-5(4H)-one (ETHIOZIN); 2-{4-[(6-chloro- 2-benzoxazolyl)-oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); N,N-dimethyl-N'-(3-trifluoromethylphenyl)-urea (FLUOMETURON); 1-methyl-3-phenyl-5-(3-trifluoromethylphenyl)-4-pyridone (FLURIDONE); [(4-amino-3,5-dichloro-6-fluoro-2-pyridin-yl)-oxy]-acetic acid or its 1-methylheptyl ester (FLUROXYPYR); 5-(2-chloro-4-trifluoromethyl-phenoxy)-N-methylsulphonyl-2-nitrobenzamide (FOMESAFEN); 2-{4-[(3-chloro-5-(trifluoromethyl)-2-pyridinyl)-oxy]-phenoxy}-propanoic acid or its ethyl ester (HALOXYFOP); 3-cyclohexyl-6-dimethylamino-1-methyl-1,3,5-triazine-2,4-dione (HEXAZINONE);methyl2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethylpyridine-3-carboxylic acid (IMAZETHAPYR); 3,5-diiodo-4-hydroxybenzonitrile(IOXYNIL);N,N-dimethyl-N'-(4-isopropylphenyl)-urea (ISOPROTURON); (2-ethoxy-1-methyl-2-oxo-ethyl 5-[2-chloro-4-(trifluoromethyl)-phenoxy]-2-nitrobenzoate (LACTOFEN); (2-methyl-4-chlorophenoxy)-acetic acid (MCPA); (4-chloro-2-methylphenoxy)propionic acid (MCPP); N-methyl-2-(1,3-benzothiazol-2-yloxy)-acetanilide(MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide(METOLACHLOR); 2-{[[((4-methoxy-6-methyl-1,3,5-triazin-2-yl)-amino)-carbonyl]-amino]sulphonyl}-benzoic acid or its methyl ester (METSULFURON); S-ethyl N,N-hexamethylenethiocarbamate (MOLINATE); 1-(3-trifluoromethylphenyl)-4-methylamino-5-chloro-6-pyridazone (NORFLURAZON); 4-(di-n-propylamino)-3,5-dinitrobenzenesulphonamide (ORYZALIN); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); 3-(ethoxycarbonylaminphenyl) N-(3'-methylphenyl)-carbamate (PHENEMEDIPHAM); 2-chloro-N-isopropylacetanilide (PROPACHLOR); isopropyl N-phenyl-carbamate (PROPHAM); O-(6-chloro-3-phenylpyridazin-4-yl) S-octyl thiocarbonate (PYRIDATE); ethyl 2-[4-(6-chloro-quinoxalin-2-yl-oxy)-phenoxy]-propionate (QUIZALOFOP-ETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-sulphonyl]-thiophene -2carboxylate (THIAMETURON); S-[(4-chlorophenyl)-methyl]-diethylcarbamothioate (THIOBENCARB); S-(2,3,3-trichloroallyl) N,N-diisopropylthiolcarbamate (TRIALLATE); 2,6-dinitro-4-trifluoromethyl-N,N-dipropylaniline (TRIFLURALIN); are also possible. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.005 and 2 kg per ha.

The preparation and use of the active compounds according to the invention can be seen from the following examples.

PREPARATION EXAMPLE

Example 1

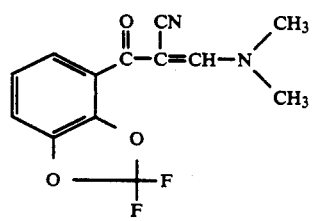

13.1 g (0.059 mol) of 2,2-difluoro-1,3-benzodioxol-4-carboxylic acid chloride are dissolved in 75 ml of dioxane. 5.7 g (0.059 mol) of N,N-dimethylaminoacrylonitrile are added dropwise to this solution at room temperature. The reaction mixture is stirred for one hour at room temperature and 16 hours at reflux temperature. After cooling, the solid substance is filtered off with suction, and the mother liquor is evaporated under reduced pressure. The residue is taken up in dichloromethane, and the mixture is washed with water and dried. The residue which remains after the solvent has been distilled off is stirred with diisopropyl ether and dried.

12.3 g (74% of theory) of 2,2-difluoro-1,3-benzodiox-4-yl-1-cyano-2-dimethyl-amino-vinyl ketone of melting point of 89° C. to 90° C. are obtained.

The compounds of formula (I) listedin the following Table 2 can also be prepared, for example, analogously to Example 1 and in accordance with the general statements on carrying out the processes according to the invention.

TABLE 2

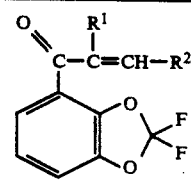

| Example | $R^1$ | $R^2$ | $^1$H-NMR* |
|---|---|---|---|
| 2 | —CO$_2$CH$_3$ | —N(CH$_3$)$_2$ | 2,31; 2,86; 3,55 |

TABLE 2-continued

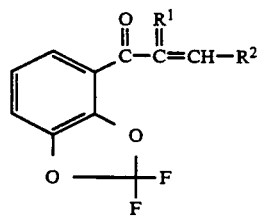

| Example | $R^1$ | $R^2$ | $^1$H-NMR* |
|---|---|---|---|
| 3 | —$CO_2C_2H_5$ | —$N(CH_3)_2$ | 0,94; 2,89; 3,32; 4,00 |

*The $^1$H-NMR spectra were recorded in deuterochloroform (CDCl₃) or hexadeuterodimethylsulphoxide (DMSO-d₆) using tetramethylsilane (TMS) as the internal standard. The chemical shift is stated as the δ value in ppm.

EXAMPLE A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 1 of water/ha. After three weeks, the degree of damage to the plants is rated in % damage in comparison to the development of the untreated control. The figures denote:

0% = no action (like untreated control)
100% = total destruction

In this test, a clearly superior activity and crop plant selectivity compared with the prior art is shown, for example, by the compound of Preparation Example 1.

EXAMPLE B

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity and crop plant selectivity compared with the prior art is shown, for example, by the compound of Preparation Example 1.

EXAMPLE C

Venturia test (apple) / protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown by the compounds of Preparation Examples.

It will be appreciated that the instant specification is set forth by way of illustration and not limitation, and that various modifications and changes may be made without departing from the spirit and scope of the present invention.

What is claimed is:

1. A substituted 2,2-difluoro-1,3-benzodioxyl-4-ketone of the general formula (I)

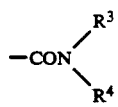

in which
$R^1$ represents —CN; —$CO_2R^5$ or

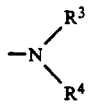

where
$R^3$ and $R^4$ in each case independently of one another represent hydrogen, alkyl, alkenyl, alkylcarbonyl, formyl, phenylalkyl optionally monosubstituted or disubstituted by fluorine, chlorine, bromine, methyl, methoxy, trifluoromethyl or trifluoromethoxy, or naphthylalkyl,
$R^5$ represents alkyl and
$R^2$ represents $$-N\begin{matrix}R^3\\R^4\end{matrix}$$

where

R³ and R⁴ have the abovementioned meaning.

2. A substituted 2,2-difluoro-1,3-benzodioxyl-4-ketone according to claim 1, in which R¹ represents —CN; —CO₂R⁵ or

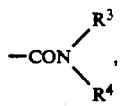

where

R³ and R⁴ in each case independently of one another represent hydrogen, straight-chain or branched alkyl having 1 to 4 carbon atoms, straight-chain or branched alkenyl having 2 to 4 carbon atoms, straight-chain or branched alkylcarbonyl having 1 to 4 carbon atoms in the alkyl group, formyl, or benzyl which optionally monosubstituted or disubstituted by fluorine, chlorine, bromine, methyl, methoxy, trifluoromethyl or trifluoromethoxy and R⁵ represents straight-chain or branched alkyl having 1 to 4 carbon atoms and R² represents

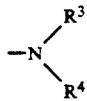

where

R³ and R⁴ have the abovementioned meaning.

3. A substituted 2,2-difluoro-1,3-benzodioxyl-4-ketone according to claim 1, in which R¹ represents —CN; —CO₂R⁵ or

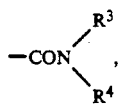

where

R³ and R⁴ in each case independently of one another represent hydrogen, methyl, ethyl, n- or i-propyl, vinyl, allyl, methylcarbonyl, ethylcarbonyl, formyl or benzyl and R⁵ represents methyl or ethyl and R² represents

where

R³ and R⁴ have the abovementioned meaning.

4. A compound according to claim 1, wherein such compound is 2,2-difluoro-1,3-benzodiox-4-yl-1-cyano-2-dimethylamino-vinylketone of the formula

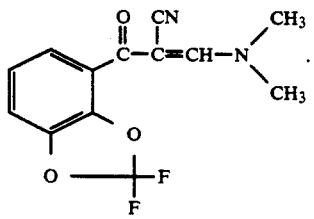

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is 2,2-difluoro-1,3-benzodiox-4-yl-1-cyano-2-dimethyl-amino-vinylketone.

* * * * *